US00PP16862P3

(12) United States Plant Patent
Beineke

(10) Patent No.: US PP16,862 P3
(45) Date of Patent: Jul. 25, 2006

(54) WHITE OAK TREE NAMED 'AFTO-1'

(50) Latin Name: *Quercus alba*
Varietal Denomination: AFTO-1

(75) Inventor: Walter F. Beineke, West LaFayette, IN (US)

(73) Assignee: American Forestry Technologies, Inc., West Point, IN (US)

( * ) Notice: Subject to any disclaimer, the term of this patent is extended or adjusted under 35 U.S.C. 154(b) by 117 days.

(21) Appl. No.: 10/919,761

(22) Filed: Aug. 17, 2004

(65) Prior Publication Data

US 2006/0041967 P1 Feb. 23, 2006

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

PP4,149 P 11/1977 Schmidt
PP9,103 P 4/1995 Wandell
PP10,853 P 4/1999 Ludeke
PP11,431 P 6/2000 Cully

OTHER PUBLICATIONS

Ruhl, Gail (2004) "Sudden Oak Death Alert—Update" *Woodland Steward*, Spring:7.

O'Connor, Phillip (2004) "White Oak Seedling Performance: Is Seed Source Important" *Woodland Steward*, Spring:10–15.

*Primary Examiner*—Anne Marie Grunberg
*Assistant Examiner*—June Hwu
(74) *Attorney, Agent, or Firm*—Alice O. Martin; Barnes & Thornburg LLP

(57) ABSTRACT

A new and distinct cultivar of white oak tree (*Quercus alba* L.) which is distinctly characterized by extremely rapid growth rate, strong central stem tendency, and excellent straightness, thereby producing good timber qualities was discovered by the applicant near South Raub, Tippeconoe County, Ind. in a white oak planting of seedling progeny from unknown sources, although it may be a seedling from WO-43 for which a separate patent application is filed. This selection has been designated as 'AFTO-1' in records maintained by the applicant on the performance of this selection, and grafts made from the selection and will be known henceforth as 'AFTO-1'.

3 Drawing Sheets

RELATED APPLICATIONS

U.S. Ser. Nos. 10/919,902 and 10/919,974.

Latin name of the genus and species: *Quercus alba* L.

Variety: 'AFTO-1'.

BACKGROUND OF THE INVENTION

This new variety of white oak tree (*Quercus alba* L.) was discovered by the applicant near South Raub, Tippecanoe County, Ind. in a white oak planting of seedling progeny from unknown sources, although it may be a seedling from WO43, from which a separate patent application is filed. (U.S. Ser. No. 10/919,902) This selection has been designated as WO55 in records maintained by the applicant on the performance of this selection, and grafts made from the selection and will be known henceforth as 'AFTO-1'. Both parents are unknown.

Nursery-grown white oak seedlings were planted in the spring of 1994 near South Raub, Ind. White oak is generally recognized as a very slow growing tree. (O'Connor and Beineke, 2004) The seedling selected for patenting displayed unusually rapid growth and while all other trees in the plantation have had the same management (intensive weed control, fertilization and pruning), this seedling is much faster growing that the other 160 trees. In addition, it is straighter than most with smaller branch diameter and shorter branches (narrower crown width).

This tree has not been observed under all growing conditions so variations may occur as result of different growing conditions. However, although a study (O'Connor and Beineke, 2004) of white oak showed some growth rates were affected by site, and preferred sites for early growth were the sandier, drier sites, height difference of the magnitude exhibited among trees that persisted over different sites, indicated a strong genetic component to growth rate in white oak.

SUMMARY OF THE INVENTION

A new and distinct cultivar of white oak tree (*Quercus alba* L.) is distinctly characterized by extremely rapid growth rate, strong central stem tendency, and excellent straightness, thereby producing excellent timber qualities, the trait of commercial interest. 'AFTO-1' was 10 years old when discovered at a location near South Raub, Ind. 'AFTO-1' has a branch angle of 75° throughout most of its crown. Branch angle (angle of branch to main trunk of the tree) is important in ease of pruning and potential forking and large branch diameter growth. Branch angle closest to 90° is most desirable for timber purposes. Most white oaks in this planting have a branch angle of 50°, which is less desirable for timber purposes.

After the original clone was selected, and assigned an identity number of WO55 the aforesaid tree was reproduced by collecting scions from it and grafting these onto common white oak rootstocks at American Forestry Technologies, Inc., West Point, Ind. These asexual reproductions ran true to the originally discovered tree and to each other in all respects.

Color values used were from the Munsell Color Chart for Plant Tissues.

No disease or insect problems were detected.

'AFTO-1' is hardy in USDA zones 5,6,7, and 8.

BOTANICAL DESCRIPTION OF THE PLANTS

Figure 1:
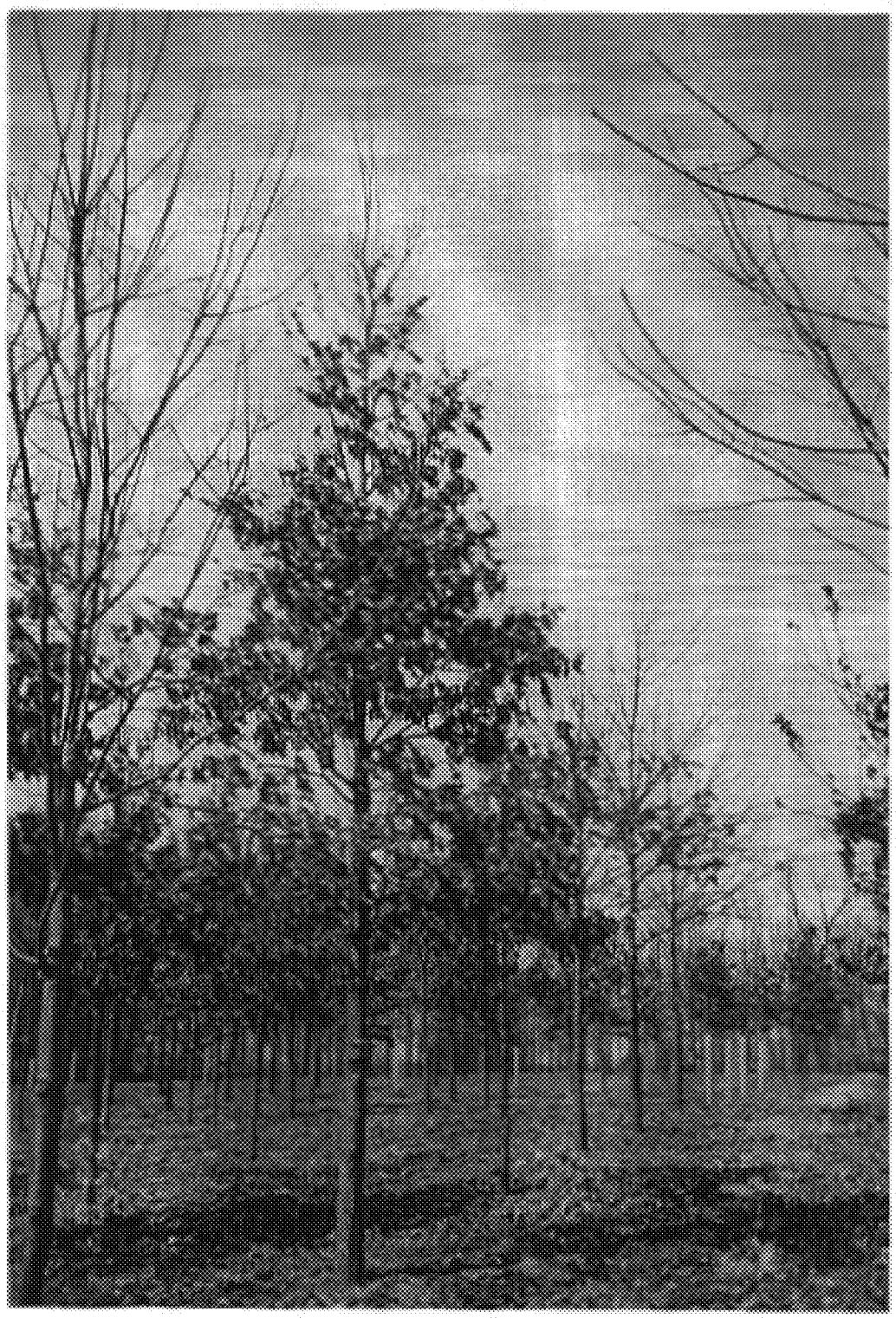
FIG. 1 is a photograph showing the timber form of 'AFTO-1'.
Figure 2:
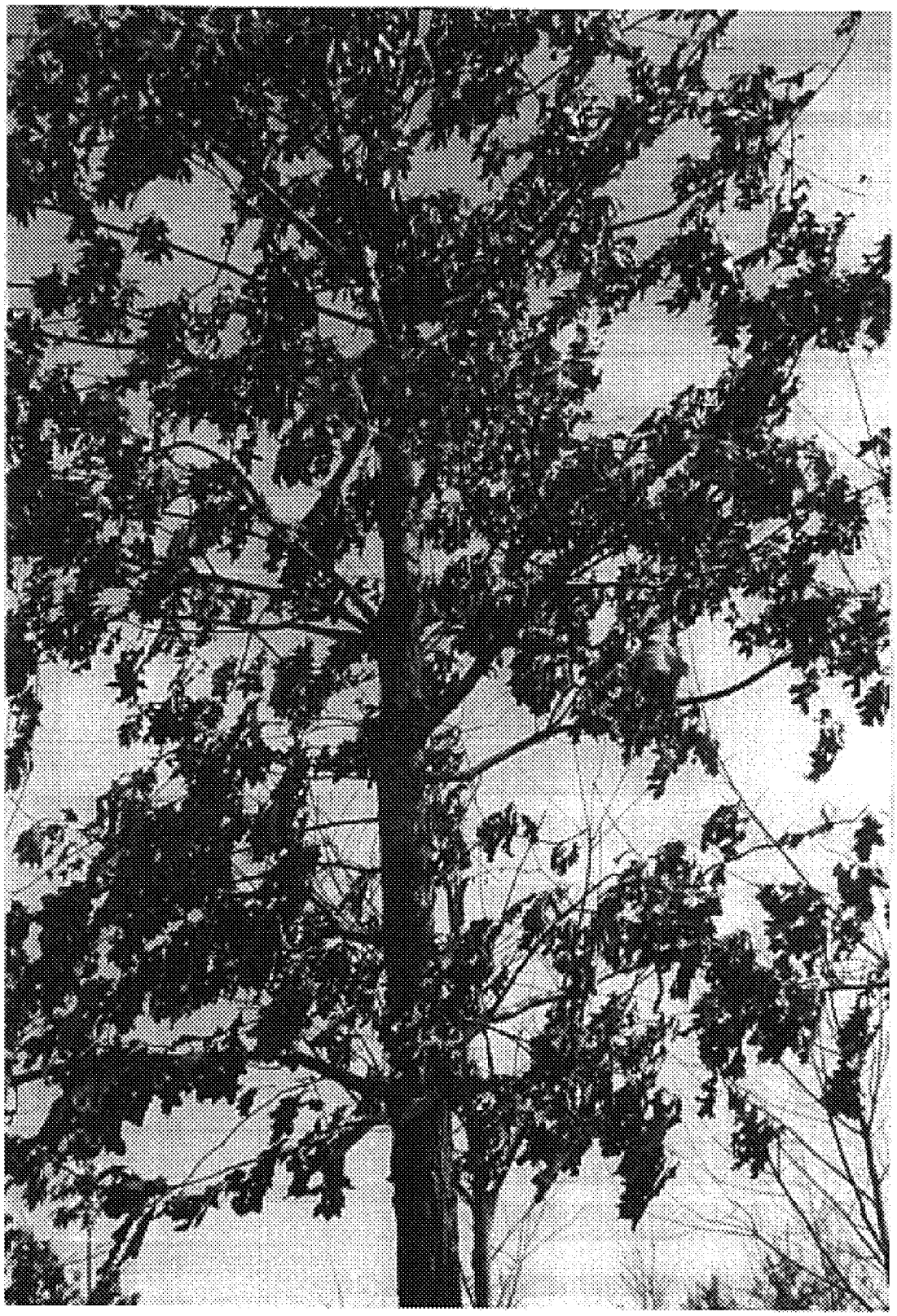
FIG. 2 is a photograph of the branch angle of 'AFTO-1'.
Figure 3:
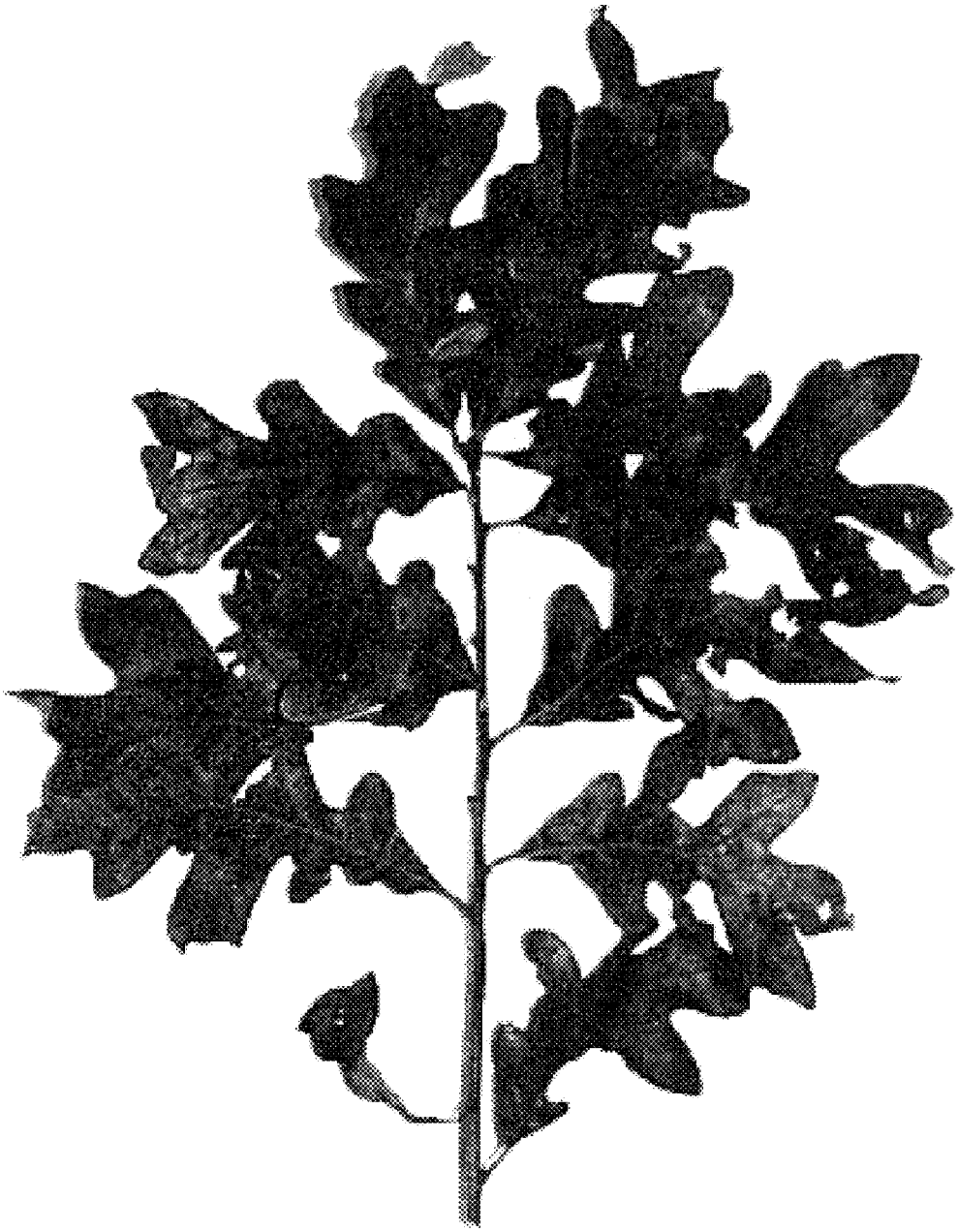
FIG. 3 is a photograph showing the leaves of 'AFTO-1'.

The botanical details of this new and distinct variety of white oak tree are as follows. Comparisons for some traits can only be made among 'AFTO-1' 'AFTO-2' (U.S. Ser. No. 10/919,902) and 'AFTO-3' (U.S. Ser. No. 10/919,574) because no other comparable trees were measured.

Tree:

*Size.*—Large, 27 ft. at 10 years; crown diameter of 12 ft. — somewhat narrow compared to other white oaks close to this height which have a crown diameter of 15 ft.

*Vigor.*—Vigorous.

*Growth rate.*—Very rapid, 96.1% larger in diameter than the average of the plantation consisting of 160 white oak trees, planted the same year on the same land. Diameter at 4½ feet above the ground at 10 years was 5.0 inches for an average growth rate of 0.50 inches per year.

*Form.*—Excellent timber form. 'AFTO-1' rates 1 on a 1 to 5 scale. Stem form was 43.5% better than the average (1.77) of the entire plantation. Stem form was obtained by subjectively rating the straightness of the main stem on a scale of 1 to 5 with 1 representing a perfectly straight stem; 2, slight crook or deviation of the central stem (no crooks); 3, about average straightness; 4, several severe crooks or a single fork; and 5, a very crooked, forked and/or leaning central stem.

*Branch and trunk color.*—One year old branches, deep reddish — 5R3/2 on the Munsell Color Chart for Plant Tissues; Older branches, dark yellow-green — 7.5GY4/2 on the Munsell Color Chart for Plant Tissues; mature trunk and branches, mottled grays — 7.5YR5/2 on the Munsell Color Chart for Plant Tissues.

*Branch and trunk characteristics.*—One year old branches, slender, glabrous; older branches, smooth; mature trunk and branches, flaky, loose edges.

*Internode length.*—Average; 1.4 inches.

*Branch lenticels.*—Light yellow-gray — 2.5Y8/2 on the Munsell Color Chart for Plant Tissues. Lenticels are round and average 0.028 inches in diameter.

*Branch angle.*—Average, 75°. Most white oaks average 50°.

Leaves:

*Leaves.*—Size — Large; average length including petiole — 7.73"; average width 4.17". Leaf apex — rounded. Leaf base — acute. The leaves of 'AFTO-1' are much larger than 'AFTO-2' (U.S. Ser. No. 10/919,902) or 'AFTO-3' (U.S. Ser. No. 10/919,574). 'AFTO-1' leaves average ½ inches wider and nearly 2 inches longer than 'AFTO-2'. 'AFTO-1' averages 1⅓ inches wider and over 2½ inches longer than 'AFTO-3'. The leaf base of 'AFTO-1' is not as acute as 'AFTO-2' and is about the same as 'AFTO-3'.

*Thickness.*—Thick.

*Texture.*—Upper surface, smooth, glabrous; Lower surface, glabrous with white bloom.

*Margins.*—Rounded and entire.

*Color.*—Upper Surface — dark green (2.5G4/4 by the Munsell Color Chart for Plant Tissues); Lower surface — light green (5GY5/4 on the Munsell Color Chart for Plant Tissues).

*Average distance between sinuses at leaf center.*—1.38". The sinuses of 'AFTO-1' (1.38 inches — average distance between sinuses) are not as deep as 'AFTO-2' (0.93 inches) or 'AFTO-3' (0.78 inches).

*Average number of lobes.*—6.8.

*Lobes.*—Rounded, typical of species. Even though the leaves of 'AFTO-1' are larger, it has fewer lobes (6.8) than 'AFTO-2' (7.0) or 'AFTO-3' (7.8).

*Petioles.*—Length — 0.64"; Color — reddish (10R4/4 on the Munsell Color Chart for Plant Tissues). 'AFTO-1' has short petioles (0.64 inches) compared to its leaf length and the petioles are shorter than 'AFTO-2' (0.78 inches) and longer than 'AFTO-3' (0.52 inches).

Buds:

*Buds.*—Typical of species — rounded, many imbricate scales, glabrous, larger than average — 0.30"; Color — brownish red (2.5YR4/8 on the Munsell Color Chart for Plant Tissues). The buds of 'AFTO-1' are longer than either 'AFTO-2' or 'AFTO-3'.

*Acorn.*—Not old enough to produce acorns.

*Flowering habit.*—Not old enough to produce flowers.

| | LEAVES | | | | | |
|---|---|---|---|---|---|---|
| | Length (inches) | Width (inches) | Distance between sinuses (inches) | Number of lobes | Petiole Length (inches) | BUDS Length (inches) |
| AFTO-1 | 7.73 | 4.17 | 1.38 | 6.80 | 0.64 | 0.30 |
| AFTO-2 | 5.88 | 3.62 | 0.93 | 7.00 | 0.78 | 0.20 |
| AFTO-3 | 5.10 | 2.78 | 0.78 | 7.80 | 0.52 | 0.21 |

DOCUMENTS CITED

O'Connor, Philip and Beineke, Walter F. (2004) "White Oak seedling performance: is seed source important?" *Woodland Steward,* vol. 13, no. 1, pp. 10–11, 13 and 15.

I claim:

1. A new and distinct cultivar of white oak tree, *Quercus alba* L. named 'AFTO-1' substantially as illustrated and described, which has excellent timber quality, extremely rapid growth rate, strong central stem tendency, and excellent straightness.

* * * * *